US007541590B2

(12) United States Patent
Croft et al.

(10) Patent No.: US 7,541,590 B2
(45) Date of Patent: Jun. 2, 2009

(54) EXTENDING THE DYNAMIC RANGE OF THE TGS THROUGH THE USE OF A DUAL INTENSITY TRANSMISSION BEAM

(75) Inventors: Stephen Croft, Middlefield, CT (US); Susan C. Kane, Glastonbury, CT (US); Patty McClay, Killingworth, CT (US); Robert D. McElroy, Jr., Middletown, CT (US); Wilhelm F. Mueller, Meriden, CT (US); Marcel F. Villani, Ellington, CT (US)

(73) Assignee: Canberra Albuquerque, Inc., Albuquerque, NM (US)

( * ) Notice: Subject to any disclaimer, the term of this patent is extended or adjusted under 35 U.S.C. 154(b) by 18 days.

(21) Appl. No.: 11/777,860

(22) Filed: Jul. 13, 2007

(65) Prior Publication Data
US 2008/0084960 A1   Apr. 10, 2008

Related U.S. Application Data

(60) Provisional application No. 60/830,527, filed on Jul. 13, 2006.

(51) Int. Cl.
*G01T 1/164* (2006.01)
(52) U.S. Cl. .................................. 250/363.04
(58) Field of Classification Search . 250/363.01–363.1, 250/362
See application file for complete search history.

(56) References Cited

U.S. PATENT DOCUMENTS 5,155,365 A * 10/1992 Cann et al. ............. 250/363.02

5,999,588 A    12/1999  Shao et al.
6,333,958 B1   12/2001  Stewart et al.
6,791,093 B2 *  9/2004  Caldwell et al. ............ 250/395

OTHER PUBLICATIONS

Estep et al., "Tomographic Gamma Scanning to Assay Heterogeneous Radioactive Waste", 1994, Nuclear Science and Engineering, vol. 118, pp. 145-152.*
Palacios et al., "A PC-based discrete tomography imaging software system for assaying radioactive waste containers", 2003, Elsevier, Nuclear Instruments and Methods in Physics Research A, vol. 508, pp. 500-511.*
S. Croft, et al.; "Extending the Dynamic Range of the TGS Through the Use of a Dual Intensity Transmission Beam"; 47th INMM Annual Meeting, Nashville, Tennessee, USA; Jul. 18, 2006; 8 pp.

(Continued)

*Primary Examiner*—David P Porta
*Assistant Examiner*—Kiho Kim
(74) *Attorney, Agent, or Firm*—David W. Carstens; Carstens & Cahoon, LLP

(57) ABSTRACT

A method for automating and extending the density range for gamma ray attenuation correction algorithms for all classes of non-destructive assay systems including those without automated shutters or automated collimators. A system and software for implementing the method are also provided. The system features a dual-intensity transmission source and utilizes a three pass scanning protocol. The high-energy source in conjunction with a beam modulator produces a high and low energy beam. Automated software determines which beam data to use in tomographic reconstruction of an object being scanned.

17 Claims, 5 Drawing Sheets

OTHER PUBLICATIONS

Ronald M. Keyser, et al.; "A Digital Method for Dead Time Compensation in Nuclear Spectroscopy"; ESARDA Symposium, Burges, Belgium; May 9, 2001; 6 pp.

D.G. Langner, et al.; "A Large Multiplicity Counter for the Measurement of Bulk Plutonium"; Institute of Nuclear Materials Management, Naples, FL, USA; Jul. 17-20, 1994; 7 pp.

(Author Unknown); "Active Neutron Coincidence Counting Techniques for 235U Mass Determination"; ESARDA; Jul. 2005; 3 pp.

M.S. Krick, et al.; "Energy-Dependent Bias in Plutonium Verification Measuremetns Using Thermal Neutron Multiplicity Counters"; Los Alamos National Laboratory, Los Alamos, NM, USA; Report LA-UR-97-3427; Oct. 1991; 12 pp.

(Author Unknown); "Passive Neutron Coincidence Counting Techniques for Pu Mass Determination"; ESARDA; NCC; Jan. 3, 2004; 4 pp.

James E. Stewart, et al.; "New Shift-Reigster Electronics for Improved Precision of Neutron Coincidence and Multiplicity Assays of Plutonium and Uranium Mass"; Los Alamos National Laboratory, Los Alamos, NM, USA; Report LA-UR-99-4927; Oct. 25, 1999; 12 pp.

* cited by examiner

EXTENDING THE DYNAMIC RANGE OF THE TGS THROUGH THE USE OF A DUAL INTENSITY TRANSMISSION BEAM

CROSS-REFERENCE TO RELATED APPLICATIONS

This application claims the benefit of provisional Application No. 60/830,527, filed Jul. 13, 2006.

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC

Not Applicable

BACKGROUND OF THE INVENTION

1. Field of the Invention

The present invention relates to tomographic imaging. More specifically, the present invention relates to a system and method for extending the density range for tomographic imaging of potentially radioactive attenuating objects in an industrial environment.

2. Description of Related Art including information disclosed under 37 CFR 1.97 and 1.98

Radioactive waste contained in drums can be highly heterogeneous in matrix distribution and may also exhibit a non-uniform and unrelated distribution of radionuclides. Under such circumstances, accurate quantitative results can be difficult or even impossible to obtain using current tomography techniques.

Current automated production environment tomographic imaging devices produce a transmission image and an emission image of an object, such as radioactive waste drum. The transmission image is a voxel-by-voxel distribution of linear attenuation coefficients throughout the drum volume. The emission image is a voxel-by-voxel distribution of the source activity from within the drum. The transmission image data is then used to create an attenuation map which is further utilized in analyzing the emission image data and ultimately quantifying the radioactive contents of the drum.

The current techniques utilize a single transmission beam of a predetermined energy for obtaining the transmission map. This well suited for low to moderate density waste matrices of approximately 1.0 g/cc for a 55 gallon storage drum. Slightly higher densities may be achieved by using alternative approaches to the analyses. These include the uniform layer and the bulk density type analyses.

In the uniform layer approach, all the voxels in a given drum layer (or segment) are populated with the same average value of linear attenuation coefficient. In the bulk density approach all of the voxels in all the drum layers are populated with the same value of linear attenuation coefficient. Still, these analyses cannot go much beyond a density waste matrix of approximately 1.5 g/cc.

Current devices require at least 10 cps at the detector to obtain useful imaging data. If the drum being imaged were homogeneous in its matrix distribution, this would not be an issue. For a drum with a uniform density, the transmission beam could be chosen that would provide the necessary count rate to obtain useful data. However, if such a system were used to measure a drum with widely varying internal densities, the beam would likely be either too bright for areas with low density or too dim for areas with high density.

Currently, an operator must perform multiple assays when attempting to image a drum with widely varying density. First, the operator must image the drum with a low-intensity beam to prevent blinding of the detector in areas of low density. However, the beam will not penetrate the high density portions and will not produce useful data. Second, the operator must image the drum with a high-intensity beam to "punch-through" the dense regions. This will blind the detector in areas with low density and not provide useful data. Finally, the operator must combine the data in some useful way to recreate the distribution of the drum. This type of imaging is impractical and inefficient due to the time required to conduct a thorough assay. Also, the costs associated with purchase and maintenance of two transmission sources is significant.

Drums with uniform density distribution are almost never encountered in real-world imaging situations. Also, current systems can only handle low to moderate density waste matrices. Automated production environments are often required to process drums with much higher densities and sizes, making accurate assays difficult if not impossible. Accordingly, a need exists for a method and system that can extend the dynamic range of a tomographic imaging device to allow it to assay drums with a density of greater than 1.5 g/cc. Further, a need exists for a single device that can perform a thorough assay on drums from low to high density waste matrices, including drums that are too hot to handle.

BRIEF SUMMARY OF THE INVENTION

The present invention utilizes a triple pass scanning protocol, featuring a transmission source that is much stronger than what is typically used for general-purpose low-density contact-handleable waste forms. The triple-pass scanning protocol involves an emission scan, an attenuated transmission scan, and a full intensity transmission scan at each drum segment.

The attenuated transmission scan is appropriate for weakly attenuating views, such as the sides of the container. The full intensity transmission beam provides the attenuation information during more severe, highly-attenuating views. By automatically performing both transmission scans, the operator does not have to choose the appropriate beam intensity for each drum, nor repeat the assay with different transmission source settings, thus reducing measurement time. During image reconstruction, the system software determines which transmission data to use at each view according to predetermined criteria.

BRIEF DESCRIPTION OF THE SEVERAL VIEWS OF THE DRAWING(S)

The present invention will be more fully understood by reference to the following detailed description of the preferred embodiments of the present invention when read in conjunction with the accompanying drawings, in which like reference numbers refer to like parts throughout the views, wherein.

Figure 5A:
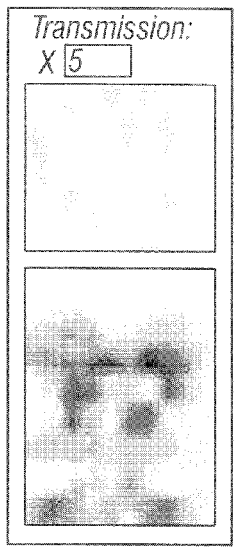
Figure 5B:
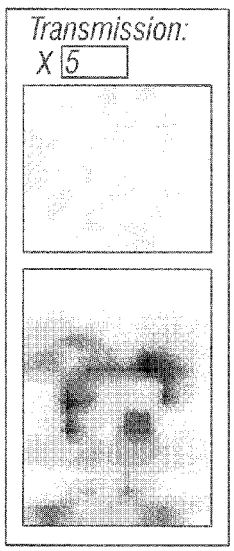
Figure 6A:
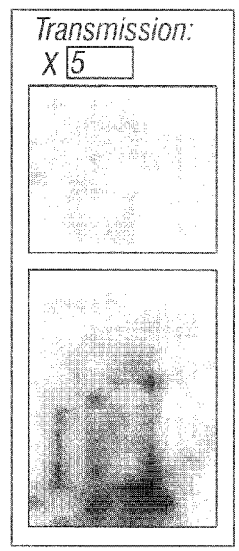
Figure 6B:
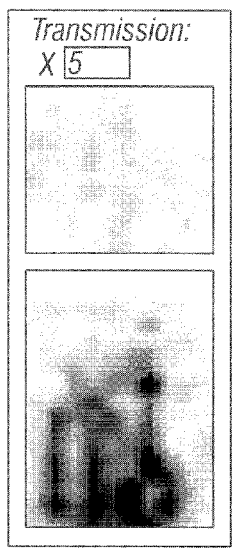
Figure 7A:
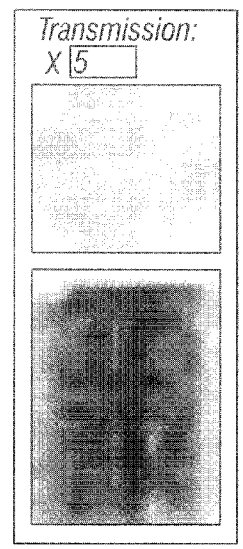
Figure 7B:
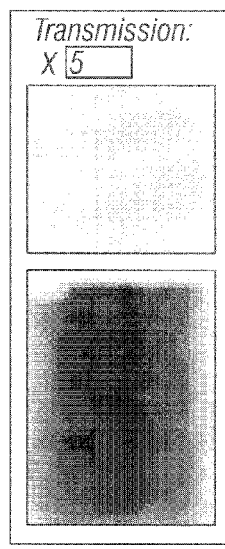
Figure 8:
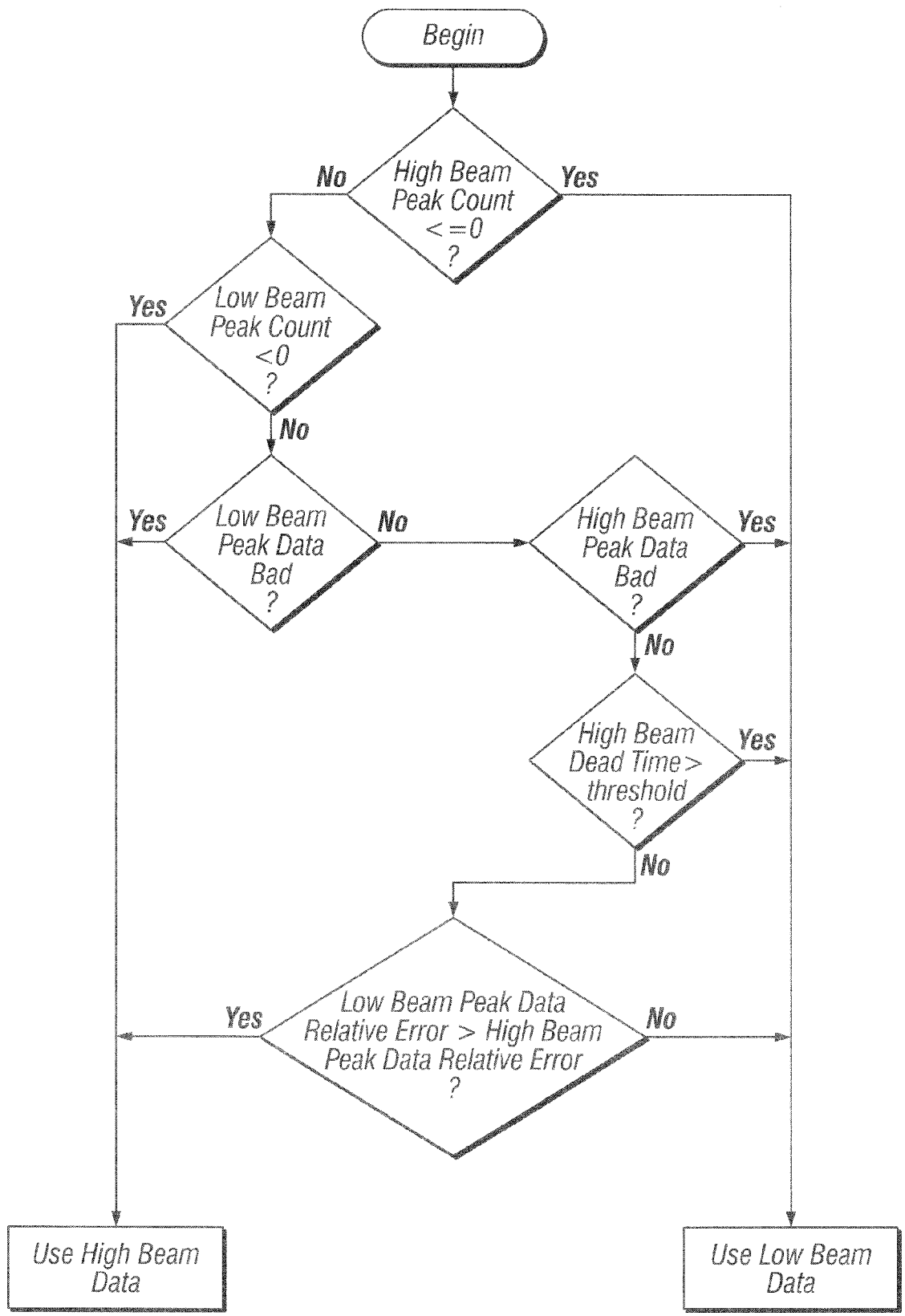
Figure 9:
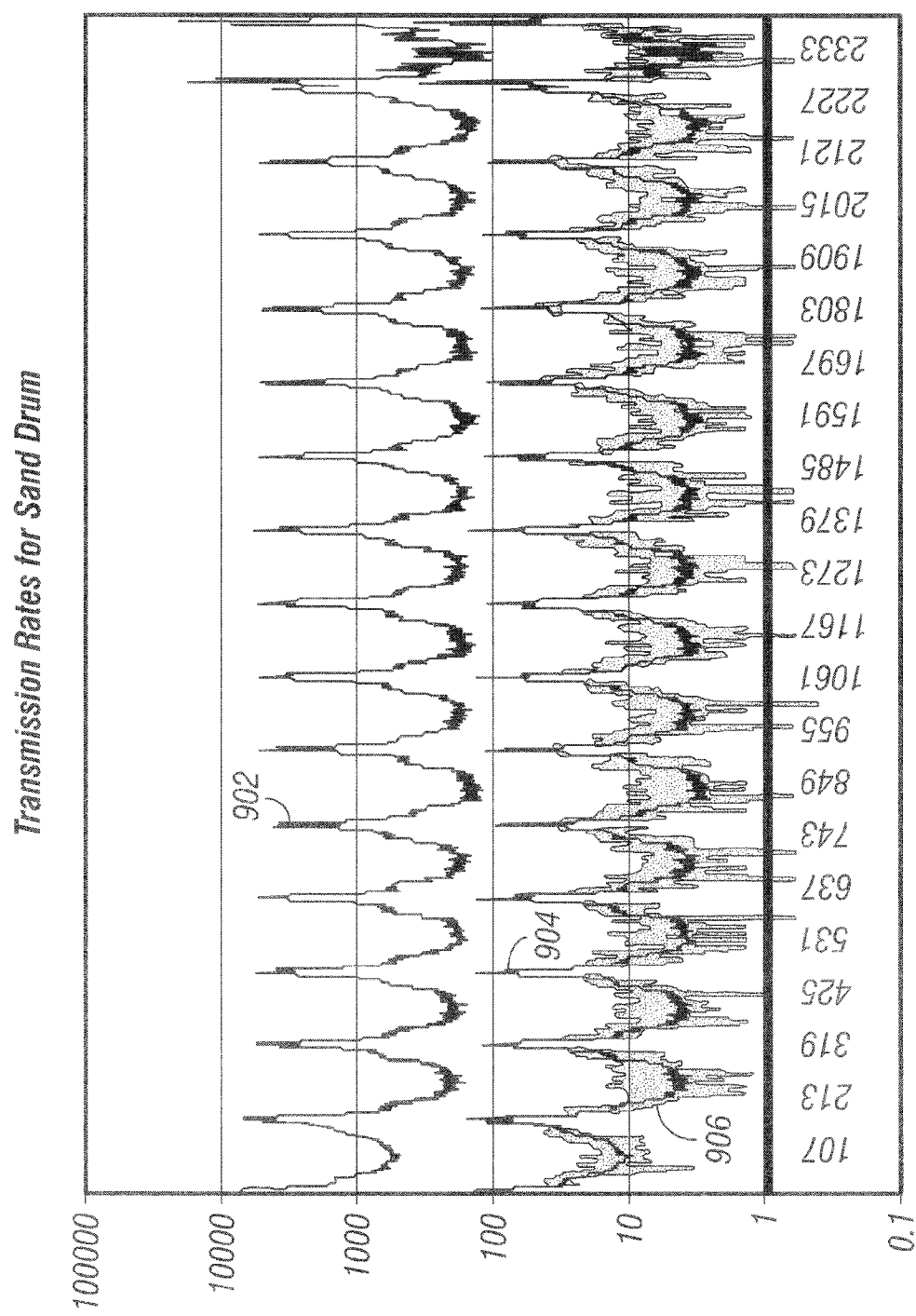

FIG. 5 features attenuation maps of the Heterogeneous Drum, comparing the use of the low-intensity beam only to the hybrid (high and low-intensity beams) transmission of the present invention;

FIG. 6 features attenuation maps of the Sample Steel Drum, comparing the use of the low-intensity beam only to the hybrid (high and low-intensity beams) transmission of the present invention;

FIG. 7 features attenuation maps of the drum filled with sand, comparing the use of the low-intensity beam only to the hybrid (high and low-intensity beams) transmission of the present invention;

FIG. 8 presents a flow diagram reflecting some of the steps taken by the system to determine whether the low or high beam data should be used, on a view by view basis; and FIG. 9 presents a graph reflecting hybrid data selected by the system in comparison with the high beam and low beam data obtained from measurements of a sand drum.

All figures are simplified and drawn for ease of explanation of the basic teachings of the present invention only; the extensions of the figures with respect to number, position, relationship, and dimensions of the parts to form the preferred embodiment will be explained or will be within the skill of the art after the following teachings of the present invention have been read and understood. Further, the exact dimensions and dimensional proportions to conform to specific force, weight, strength, and similar requirements will likewise be within the skill of the art after the following teachings of the present invention have been read and understood.

DETAILED DESCRIPTION OF THE INVENTION

Obtaining a high quality attenuation map is a prerequisite to obtaining an accurate tomographic gamma scanner (TGS) assay. For highly attenuating items, counting precision is a limiting factor for some views. The dynamic range can be extended by using a strong, high-energy source in conjunction with a beam modulator allowing high and low transmission modes. For modest attenuation, the weak or low beam intensity is used to obtain transmission factors. When count rates are too low to be viable, the system automatically uses the high beam data. Ordinarily, the high beam would saturate the detector due to excessive dead-time and pile up; hence, the transmission data from the high beam cannot be used throughout the range.

Implementation

Figure 1:
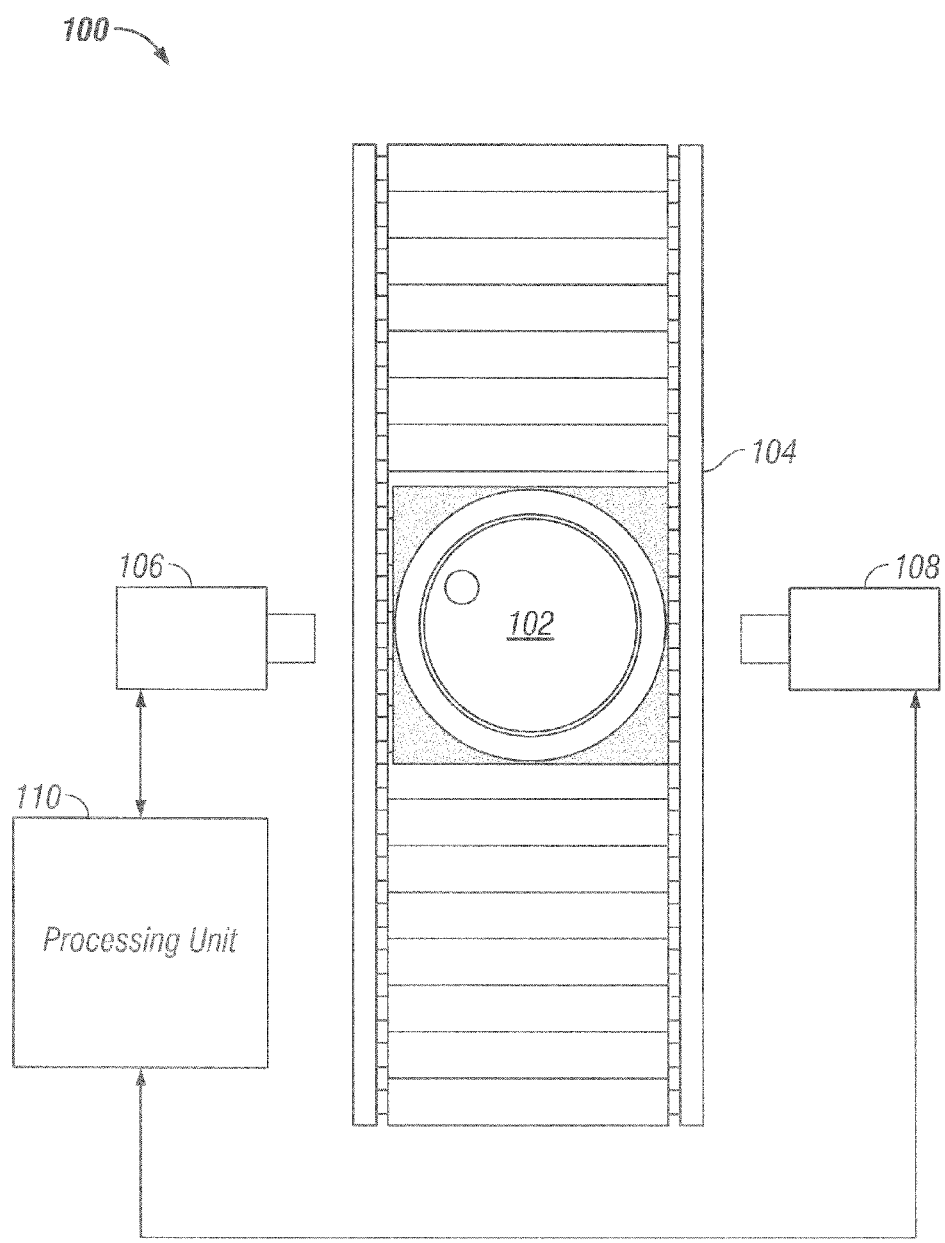
FIG. 1 is block diagram of an embodiment of the present invention as it is used to conduct tomographic imaging of a drum containing radioactive waste in an automated production environment.

FIG. 1 depicts a basic block diagram 100 of the invention in its present embodiment. In a typical automated production environment, a drum containing a heterogeneous distribution of radioactive waste 102 passes before the tomographic gamma scanner transmission source housing 106 and the detector housing 108 on a conveyor apparatus 104. The drum 102 is positioned before the transmitter housing 106 and detector housing 108 where its contents are imaged and the data is processed by a central processing unit 110.

Data acquisition occurs in the present embodiment while the drum is rotating and translating (horizontally) between the transmitter and detector. While the drum is moving, a count is taken for a fractional period. The present embodiment count period is approximately 0.75 seconds. This is considered to be a "grab" or a "view" of the drum. There are approximately 150 grabs per segment. Following this period, the spectrum data is saved, the analyzer cleared, and another grab is taken. One skilled in the art will appreciate that the count length and number of grabs per segment can vary without exceeding the scope of the present invention.

The preferred embodiment of the present invention utilizes a single strong transmission source with only one high-energy line. Other embodiments may feature a single strong transmission source with more than one high-energy line. For a multi-line source with a spectrum of energies, the soft components are preferentially removed at modest item thicknesses. A mono-energetic source has the advantage that the rates are concentrated into a few useful peaks. Therefore, the "straight through" counting rate capability is not wasted on lines that will not penetrate the attenuating object.

The present embodiment utilizes a Co-60 source in the 250 mCi range. While Co-60 was chosen in this embodiment, a variety of others can be used, preferably one with a long half life and lines that extend the range of energies of interest. The source store was redesigned with additional shielding to maintain the dose rate on contact at all accessible places to less than 2 mSv/h in soft tissue.

Co-60 was chosen as the transmission source because of its pair of high-energy gammas. Traditionally, Eu-152 is preferred because of its wide energy range of gammas that allow for empirical determination of the attenuation of the energy range. However, for moderate to severely attenuating items only high-energy gammas will penetrate. Thus, most of the intensity of the transmission source does not penetrate the item in the case of Eu-152. Furthermore, if the penetrating lines from Eu-152 at 1112 and 1408 keV are considered somewhat analogous to the lines at 1173 and 1332 keV from Co-60, then the ratio of count-rate available from the high activity Co-60 source is a factor of over 100 times greater than the strongest general purpose Eu-152 source. This increase extends the range of the density of items of interest to 2.5-3.5 g/cc. Consequently, rates are viable for more attenuating items and/or, for some classes of waste, when higher activities are present in the item.

The drawback to using Co-60, however, is that the behavior of the transmission factor as a function of energy can no longer be extracted from the observed transmission data and the materials basis set ("MBS") method of interpolating the attenuation map can no longer be applied. This problem is circumvented by allowing the user to select a single representative material, referred to as the Z-effective ("$Z_{eff}$"), which is used to provide the energy dependence of the (mass) attenuation coefficient. In practice, within the overall Total Measurement Uncertainty ("TMU") this turns out not to be a major source of bias for gamma ray energies above about 200 keV, which is away from the influence of the strong atomic number dependence of the photoelectric cross section.

The source transmission beam "cone" is defined by the aperture in the source housing (store). The present embodiment also features a diamond shaped collimator, which typically is of the order of the crystal size across the flats of the diamond opening, allowing the source to remain fully illuminated. This maximizes the counting rate in the detector for a given source activity. A shutter means is also provided with the store to allow the source radiation to be "turned off" (i.e., contained).

In the present embodiment, a moveable attenuator is placed before the transmission store opening to allow the transmission beam to be modulated. In this embodiment, cylindrical sintered tungsten was chosen for its attenuating capabilities. When both the attenuator and the shutter are down (the gravity-selected position in the case of power failure), the beam is switched off and the peak counting rates in the detector are close to background rates. With only the shutter raised, the beam is in Low-Intensity mode. With both the shutter and the attenuator raised, the beam is in High-Intensity mode.

The Tungsten cylinders are oversized radially to quell few scattered radiation from reaching the detector. In this embodiment, the combined length of the shutter and attenuator is about 220 mm. One skilled in the art will appreciate that the length of the attenuator may be trimmed for a given detector-source combination to take best advantage of the dynamic range without exceeding the scope of the present invention. Other attenuating means may be chosen without exceeding the scope of the invention. These include collimators, filters, slot devices, diaphragms, and the equivalents.

In another embodiment, an additional attenuator shields the detector to prevent an extremely hot object being assayed from blinding the detector with its emitted radiation. In such a situation, the attenuator could be a cylindrical tungsten filament, a collimator, a filter, a slot, a diaphragm, or some equivalent. If used, the detector attenuator would likely cause the low transmission beam to be too weak to produce effective counts. However, the high-beam data should be sufficient at all densities to produce good imaging data.

Characterizing the High to Low Beam Ratio

During initial setup and for periodic calibration of the embodiment of the present invention, the high to low beam ratio must be established. However, the count rate of the transmission beam is not measurable when the beam is unattenuated. This is due to the limitations in the capability of the electronic counting circuitry given that the high beam is designed to "punch through" dense waste items. Therefore, the ratio of the high to low beam must be calculated without directly measuring the high beam intensity.

First, the count rate of the transmission beam in Low-Intensity-Beam mode (i.e. with the sintered Tungsten attenuator or an equivalent in place) is measured directly. Then, an additional attenuator (such as a sand filled drum) is introduced between the detector and the transmission beam. The Low-Intensity count-rate, x, is measured, obtaining:

$$x \pm \sigma_x = f \cdot I_L \qquad (1)$$

where f is the attenuation factor through the item introduced and $I_L$ is the unattenuated count rate of the transmission beam in Low-Intensity-Beam mode. Without moving the attenuating item, the count rate, y, is measured in High-Intensity-Beam mode to yield:

$$y \pm \sigma_y = f \cdot I_H \qquad (2)$$

where $I_H$ is the unattenuated count rate of the transmission beam in High-Intensity mode. These measurements should be collected for as long a period as possible to ensure adequate statistics.

From these rates, which may be fully corrected for deadtime using the pulser method and their associated standard deviation estimates (and, if necessary, peak background), the ratio between the two beam strengths, r, for each transmission energy is estimated as:

$$r = \frac{y}{x} \pm \sigma_r \qquad (3)$$

where $$\sigma_r = r \sqrt{\left(\frac{\sigma_x}{x}\right)^2 + \left(\frac{\sigma_y}{y}\right)^2}$$

Thus, $I_H$ is determined for each transmission energy by:

$$I_H = r \cdot I_L \pm \sigma_{I_H} \qquad (4)$$

where $$\sigma_{I_H} = I_H \sqrt{\left(\frac{\sigma_r}{r}\right)^2 + \left(\frac{\sigma_{I_L}}{I_L}\right)^2}$$

The estimates of $I_L$ and $I_H$ are thus correlated but, in principle, the uncertainty on r can be arbitrarily small by decreasing the uncertainty on $I_L$ and $I_H$. In practice, $I_L$ can be determined at the beginning of each assay, which can also serves as a check on system efficiency, resolution, and other factors.

The approach outlined above is less prone to systematic uncertainty, such as from taking the book value of the mass attenuation coefficient of the material, than calculating $I_H$ directly via Equation (2). The selection of an appropriate item to provide a suitable attenuation factor, f, is open to experimentation for a given system so that suitable counting rates can generate suitable precision in $I_H$ in a viable measurement time. It is also advocated that several different items, different density drums, or other items (e.g. a sand filled drum, a heavy steel drum, a Pb-block) be used for this purpose so that several estimates for $I_H$ can be obtained. This may alleviate potential sources of random reproducibility and any potentially small but unrecognized counting rate dependences that may be present.

The important parameters for the system of the present embodiment to store are the Low-Intensity Beam count rate, $(I_L \pm \sigma_{I_L})$, the reference date, and the transmission beam ratio, $(r \pm \sigma_r)$. The Low-Intensity beam count rate is directly measured at the start of each assay, whereas the reference date is a primary system parameter. The transmission beam ratio is energy dependent, is determined off-line, and may be entered as a primary system parameter. This value is expected to be practically independent of detector collimator opening and detector to transmission source separation for a given attenuator. The High-Intensity beam count rate, $(I_H \pm \sigma_{I_H})$, should then be calculated and held internally as a derived parameter according to the method described above.

Prior to each assay, the present embodiment repeats the low-intensity transmission beam energy measurement with no attenuating item in place. This is done to normalize the count rate values during an assay. Using the above equations 1 through 4, the system can then determine the high intensity transmission beam energy.

Monte Carlo Replicate Method

In applying the Monte Carlo Replicate ("MCR") method to the problem of estimating the statistical assay uncertainty, it is important that the raw count data be perturbed rather than using a scaled rate. In this way, the scatter in the data characteristic of the inherent randomness in the counting statistics will be taken into account in a natural way.

In the assay protocol of the present embodiment, the unattenuated count rate in the Low-Intensity mode, $I_L$, is determined with the drum moved to the side as part of the assay sequence. Thus, I is calculated as:

$$I = \frac{C}{I_0}\left[\text{nominally} \pm I \sqrt{\left(\frac{\sigma_C}{C}\right)^2 + \left(\frac{\sigma_{I_0}}{I_0}\right)^2} \text{ at 1-sigma}\right] \quad (5)$$

where $I_0$ is either $I_L$ or $I_H$ and C is the net peak count rate. The selection of the I-value from the low beam or high beam scan is based principally on the dead-time during the grab, as estimated from the reference pulser peak, being below a user selectable threshold and the statistical viability of the transmission data.

The MCR method statistically perturbs the number of counts in the background ROI(s) and in the peak ROI using Poisson distribution, thus allowing the number of net counts to fluctuate randomly. In a way, this is analogous to repeating the assay. The perturbed counts can thus be propagated through the entire analysis process to evaluate the impact on the assay result.

The difference between MCR for a standard TGS and the dual-intensity TGS is that MCR must include the estimate of the high beam rate, which contains an additional source of uncertainty through the multiplier, r, which is common to all views. Thus, another tier of perturbation is required. In essence, the assay must be performed (on the unperturbed view data) using three values of r corresponding to the best estimate value and the value $\pm\sigma_r$. The 1-sigma systematic assay uncertainty associated with the uncertainty in the r-value is obtained from half the spread in the two assay values obtained using $(r-\sigma_r)$ and $(r+\sigma_r)$.

There is an analogous effect already present in the standard TGS scan approach in that the estimate of $I_0$ (=$I_L$) is subject to a counting uncertainty that affects all views. It is important to realize, therefore, that during an assay r and $I_L$ are independent, (i.e., the characterization measurement that leads to the estimate of r is separate from the unattenuated count rate $I_L$ measured at the start of an assay). Thus, an analysis should be performed with $I_L$ and $(I_L\pm\sigma_{I_L})$ and with r and $(r\pm\sigma_r)$ to obtain the uncertainty contributions due to these two sources.

Next, replicates should be run to perturb the net peak rates, keeping within the original dead-time selection or allowing the decision criteria to be flipped. In this way, both the systematic and random counting uncertainties are properly accounted for. In practice, knowledge of the transmission beam properties is typically very good in comparison to other sources of uncertainties that contribute to assay uncertainty.

Selection of Beam Data

The system of the present embodiment, on a view by view basis, tests both the high and low beam data to determine which should be used. FIG. 8 presents a flow diagram reflecting details of these decisions. To override a beam and force the system to choose the other, the overridden beam data can be set to a negative number. First, the system determines if the beam data is valid. The low beam peak data is tested for validity first. This test compares the net transmission count rate to a threshold and the reference peak rate to zero. If this fails, the high beam data is used. If not, the high beam peak data validity is tested in a similar fashion. If it fails, the low beam data is selected. If it passes, the high beam dead time is checked against a dead time threshold. If it fails, the low beam data is used. If it passes, the low beam peak data relative error is checked against the high beam peak data relative error. If the low beam error is higher, the high beam data is used and vice-versa. This test is performed following each data acquisition period. Other embodiments wait until all of the high and low beam data are obtained to select which beam data to use in reconstructing the image.

Testing

Using the present embodiment, measurements were performed on three 200 l drums, each filled with a different matrix featuring eight rods of Co-60, Ba-133, and Cs-137 to simulate a radioactive distribution. The combined activities of Co-60, Ba-133, and Cs-137 for all rods were 40 µCi, 246 µCi, and 41 µCi, respectively. Assays were performed using the TGS system setup described above.

The first drum was filled entirely with sand, with holes to allow source rod placement, and had a density of about 1.6 g/cc. The next drum was filled with scrap pieces of steel, referred to as the Sample Steel Drum, with an average density of approximately 1.09 g/cc. The last drum, known as the Heterogeneous Drum, was filled with quart Plexiglas canisters filled with steel shots, sand, and walnut shells. The average density of the Heterogeneous drum was approximately 0.64 g/cc. TGS analyses were then performed on these measurements. A $Z_{\mathit{eff}}$ of 14 was chosen for the Heterogeneous Drum and the sand drum, and a $Z_{\mathit{eff}}$ of 26 was used for the Sample Steel Drum. The calibration of the system was performed using the low intensity transmission beam only on an empty drum with the same rods used in these measurements.

For comparison, the drums were analyzed in three modes: low beam transmission only, high beam transmission only, and hybrid transmission. The low beam transmission only analysis was equivalent to the capability of a standard TGS. High beam transmission only analysis was the same as for low beam only, using the full intensity of the beam for all views. Lastly, the hybrid analysis method used both beam intensities of the dual-intensity TGS of the present embodiment.

Figure 2:
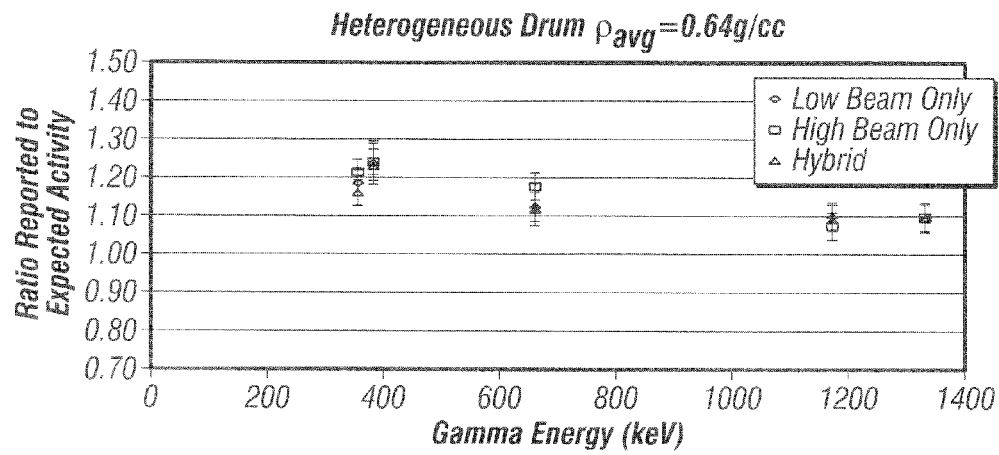
FIG. 2 is a graph of the ratio of the reported to expected activity for various gammas in a heterogeneous drum with an average density of 0.64 g/cc.
Figure 3:
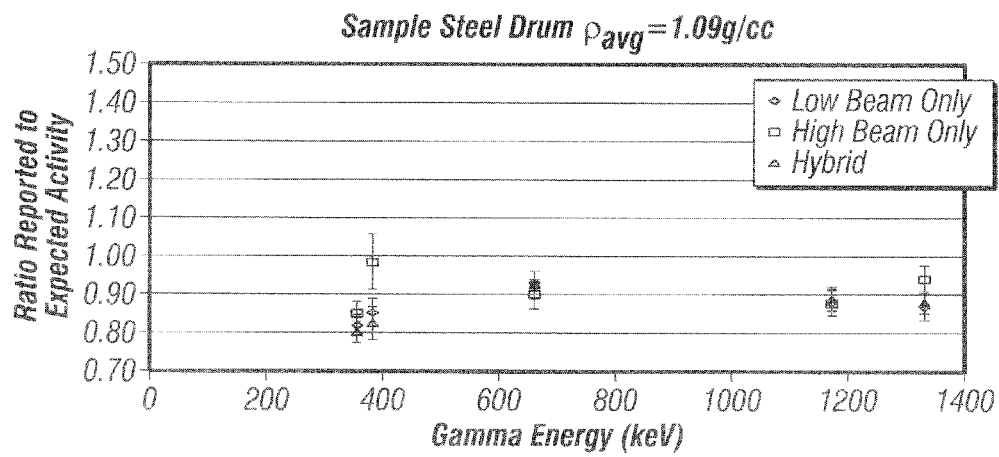
FIG. 3 is a graph of the ratio of reported to expected activity for various gammas in a sample steel drum with an average density of 1.09 g/cc.
Figure 4:
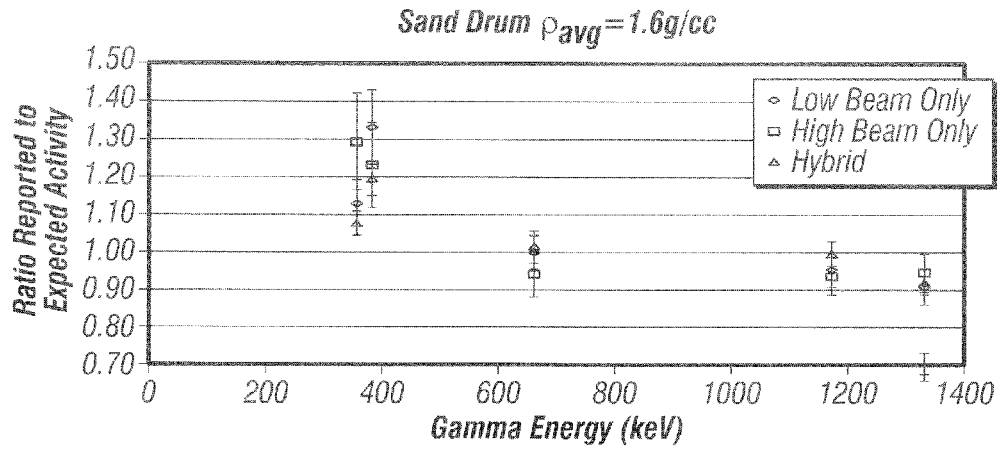
FIG. 4 is a graph of the ratio of reported to expected activity for various gammas in a drum filled with sand with an average density of 1.60 g/cc.

FIGS. 2 through 4 display the ratio of the reported to expected activities for the 356 keV and 383 keV lines from the Ba-133 rods; the 662 keV line from the Cs-137 rods; and the 1173 keV and 1332 keV lines from the Co-60 rods. A ratio of unity would indicate perfect agreement. Note the presence of the radionuclides in the transmission source data is compensated for because the emission data is used as the peaked background for the transmission.

Of further interest is the image of the attenuation map of each drum. FIGS. 5 through 7 show a two dimensional attenuation map of each of the drums for Low beam only and for hybrid transmission. FIG. 5 provides the attenuation maps of the Heterogeneous Drum. FIG. 6 provides the attenuation maps of the Sample Steel Drum; and FIG. 7 provides the attenuation maps of the sand drum. The upper part of each figure is a linear attenuation coefficient map across layer 5 of the 16 layer axial scan. The lower part is a projection of the opacity of the drum.

Using hybrid transmission, the results are within 20% of the expected except for 383 keV in the Heterogeneous Drum. The results for the Heterogeneous Drum are biased high, which is probably due to the selection of $Z_{\mathit{eff}}$. This is realistic of actual operation when the user will not know the composition of the waste matrix. In practice, the TMU will encompass the resulting uncertainty based on a range of $Z_{\mathit{eff}}$. In the Sample Steel Drum the statistics are poor for the low-energies of Ba-133; hence, the greater disagreement between those reported activities and the expected. The results for the sand drum are notable for Cs-137 and Co-60, within 10%.

The attenuation maps are more of a visual record that the hybrid transmission corrects for attenuation better than the single-intensity transmission TGS. A slight improvement can be seen in the Heterogeneous Drum. The sample steel drum attenuation map created using the hybrid scan shows more of a contrast between air and the steel than the map from the low-intensity only scan.

The improvement in the attenuation can be seen most profoundly in the comparison of the attenuation maps for the sand drum. The map created with the low-intensity transmission TGS scan has more of a checkered board pattern, indicating the source is not strong enough to penetrate the drum. The hybrid transmission map is much clearer, without the checkered board effect.

FIG. 9 shows a graph reflecting the hybrid data 904 chosen by the system versus the high beam data 902 and low beam data 906 from measurement of the sand drum. This drum provides a good example of how the system decides, view-by-view, between the high and low beam data. As can be seen by this graph, the system consistently chose the high beam data 904 over the low 906. The low was relatively weak and noisy, which made the high beam data the obvious choice. The hybrid data 904 is normalized to the low beam data 906 using the transmission ratio calculated above.

It will now be evident to those skilled in the art that there has been described herein an improved computer-based learning system that through a combination of repetitive narrative solutions and multiple choice questions greatly facilitates trainee learning, improving significantly the retention of information over existing training methods.

Although the invention hereof has been described by way of a preferred embodiment, it will be evident that other adaptations and modifications can be employed without departing from the spirit and scope thereof. For example, some of the steps in the method could be conducted manually in addition to those conducted automatically. The terms and expressions employed herein have been used as terms of description and not of limitation; and thus, there is no intent of excluding equivalents, but on the contrary it is intended to cover any and all equivalents that may be employed without departing from the spirit and scope of the invention 58,266.

We claim:

1. A method to automate and extend the density range for gamma ray attenuation correction algorithms for a non-destructive assay system, the non-destructive assay system for conducting tomographic imaging of an object utilizing a low-intensity transmission beam and a high-intensity transmission beam, the object containing potentially radioactive material, the method comprising:
   measuring the un-attenuated low-intensity beam to obtain a low-intensity un-attenuated count rate;
   introducing an attenuating object between the transmitter and detector;
   measuring the attenuated low-intensity beam to obtain a low-intensity attenuated count rate;
   determining an attenuation factor;
   measuring the attenuated high-intensity beam to obtain a high-intensity count rate;
   determining the high-intensity un-attenuated count rate;
   determining the ratio using standard deviation estimates;
   imaging the object with the low-intensity transmission beam to obtain low-beam data;
   imaging the object with the high-intensity transmission beam to obtain high-beam data;
   imaging the object by collecting passive emissions to obtain passive-emissions data;
   creating an emissions map of the object utilizing the passive-emissions data;
   convolving the low-beam and high-beam data to obtain an attenuation map of the object; and
   overlaying the emissions map with the attenuation map to obtain a quantitative radiation map of the object.

2. The method of claim 1 wherein the low-intensity transmission beam is obtained by modulating the high-intensity transmission beam.

3. The method of claim 1 wherein the low-intensity transmission beam is obtained by modulating the source using an attenuation means selected from the group consisting of a cylindrical tungsten filament, a collimator, a filter, a slot, and a diaphragm.

4. The method of claim 1, the method steps further comprising:
   utilizing an attenuation device to compensate for a highly radioactive object, wherein the attenuation device is selected from the group consisting of a cylindrical tungsten filament, a filter, a slot, and a diaphragm.

5. The method of claim 1 wherein the count rates are corrected for dead-time effects.

6. The method of claim 1 wherein the high and low beam data are compared and one is selected on a view-by-view basis.

7. The method of claim 1 wherein the high and low beam data are compared and one is selected after all beam data has been obtained.

8. A computer software program tangibly embodied in a computer readable medium, the program including machine-readable instructions executable by a computer processor to perform a method to automate and extend the density range for gamma ray attenuation correction algorithms for a non-destructive assay system, the non-destructive assay system for conducting tomographic imaging of an object utilizing a low-intensity transmission beam and a high-intensity transmission beam, the object containing potentially radioactive material, the program steps comprising:
   measuring the un-attenuated low-intensity beam to obtain a low-intensity un-attenuated count rate;
   measuring the attenuated low-intensity beam to obtain a low-intensity attenuated count rate;
   calculating an attenuation factor;
   measuring the attenuated high-intensity beam to obtain a high-intensity count rate;
   calculating the high-intensity un-attenuated count rate;
   calculating the ratio using standard deviation estimates;
   collecting the low-beam data obtained by imaging the object with the low-intensity transmission beam;
   collecting the high-beam data obtained by imaging the object with the high-intensity transmission beam;
   collecting the passive-emissions data;
   creating an emissions map of the object utilizing the passive-emissions data;
   convolving the low-beam and high-beam data to obtain an attenuation map of the object; and
   overlaying the emissions map with the attenuation map to obtain a quantitative radiation map of the object.

9. The computer program product of claim 8 wherein the count rates are corrected for dead-time effects.

10. The computer program product of claim 8 wherein the high and low beam data are compared and one is selected on a view-by-view basis.

11. The computer program product of claim 8 wherein the high and low beam data are compared and one is selected after all beam data has been obtained.

12. A system to automate and extend the density range for gamma ray attenuation correction algorithms for a non-destructive assay system, the non-destructive assay system for conducting tomographic imaging of an object, the object containing potentially radioactive material, the system comprising:
- at least one low-intensity radioactive transmission beam source;
- at least one high-intensity radioactive transmission beam source;
- at least one attenuation means;
- at least one detector; and
- a computing means, wherein the computing means is adapted to execute the program steps comprising:
  - measuring the un-attenuated low-intensity beam to obtain a low-intensity un-attenuated count rate;
  - measuring the attenuated low-intensity beam to obtain a low-intensity attenuated count rate;
  - calculating an attenuation factor;
  - measuring the attenuated high-intensity beam to obtain a high-intensity count rate;
  - calculating the high-intensity un-attenuated count rate;
  - calculating the ratio using standard deviation estimates;
  - collecting the low-beam data obtained by imaging the object with the low-intensity transmission beam;
  - collecting the high-beam data obtained by imaging the object with the high-intensity transmission beam;
  - collecting the passive-emissions data;
  - creating an emissions map of the object utilizing the passive-emissions data;
  - convolving the low-beam and high-beam data to obtain an attenuation map of the object; and
  - overlaying the emissions map with the attenuation map to obtain a quantitative radiation map of the object.

13. The system of claim 12 wherein the source is 60 Co with an activity of about 250 mCi.

14. The system of claim 12 wherein the low-intensity transmission source and the high-intensity transmission source is a single radioactive transmission source that is modulated to produce the differing intensities.

15. The system of claim 12 wherein the source comprises two distinct sources of differing transmission energies, and wherein the system selects between the two sources during an assay by shuttering one and exposing the other.

16. The system of claim 12 wherein the at least one attenuation means is selected from the group consisting of a cylindrical tungsten filament, a collimator, a filter, a slot, and a diaphragm.

17. The system of claim 12 wherein the detector comprises an attenuation means selected from the group consisting of a cylindrical tungsten filament, a filter, a slot, and a diaphragm.

* * * * *